United States Patent [19]

Sanderson et al.

[11] Patent Number: 5,169,550
[45] Date of Patent: Dec. 8, 1992

[54] SYNTHETIC LUBRICANT BASE STOCKS HAVING AN IMPROVED VISCOSITY

[75] Inventors: John R. Sanderson, Leander; Edward T. Marquis, Austin, both of Tex.

[73] Assignee: Texaco Chemical Company, White Plains, N.Y.

[21] Appl. No.: 534,080

[22] Filed: Jun. 6, 1990

[51] Int. Cl.[5] .......................................... C10M 111/02
[52] U.S. Cl. .................................... 252/52 R; 585/3; 585/20; 585/533
[58] Field of Search ...................... 585/3, 533, 258, 20, 585/533; 252/52 R

[56] References Cited

U.S. PATENT DOCUMENTS

| | | | |
|---|---|---|---|
| 2,732,408 | 1/1956 | Foote | 260/624 |
| 3,173,965 | 3/1965 | Pappas et al. | 260/667 |
| 3,432,571 | 3/1989 | Noddings et al. | 260/683.15 |
| 3,716,596 | 2/1973 | Bowls | 260/671 C |
| 3,808,134 | 4/1974 | Romine | 585/11 |
| 3,849,507 | 11/1974 | Zuech | 260/671 C |
| 4,013,736 | 3/1977 | Woo | 585/255 |
| 4,153,385 | 5/1979 | Bercik et al. | 585/459 |
| 4,351,980 | 9/1982 | Reusser et al. | 585/20 |
| 4,401,579 | 8/1988 | Kratzer | 252/17 |
| 4,409,113 | 10/1983 | Bertell | 252/42 |
| 4,480,142 | 10/1984 | Cobb | 585/458 |
| 4,531,014 | 7/1985 | Gregory et al. | 585/415 |
| 4,556,750 | 12/1985 | Cobb | 585/446 |
| 4,604,491 | 8/1986 | Dressler et al. | 585/26 |
| 4,620,048 | 10/1986 | Ver Strate et al. | 585/10 |
| 4,788,362 | 11/1988 | Kaneko | 585/10 |
| 4,827,064 | 5/1989 | Wu | 585/12 |
| 4,892,680 | 1/1990 | Ishida | 252/565 |
| 4,962,262 | 10/1990 | Winter et al. | 585/512 |
| 4,967,029 | 10/1990 | Wu | 585/12 |
| 4,968,853 | 11/1990 | Scharf | 585/10 |

FOREIGN PATENT DOCUMENTS

| | | |
|---|---|---|
| 0353813 | 7/1990 | European Pat. Off. |
| 2501224 | 9/1982 | France |
| 1489646 | 10/1977 | United Kingdom |
| 2046298 | 11/1980 | United Kingdom |

OTHER PUBLICATIONS

Purnell, "Catalysis by Ion-Exchanged Monitmirillonites," *Catalysis* Letters, p. 5 (1990), pp. 203–210.

Friedlander et al. "Organized Polymerization I. Olefins on a Clay Surface," *Journal of Polymer Science: Part C*, No. 4, pp. 1291–1301.

"Synthetic Lubricants from Internal Olefins," Process Evaluation/Research Planning Report, Chem Systems, 84-Q-1, pp. 17–45.

Adams, "Synthetic Organic Chemistry Using Pillared, Cation-Exchanged and Acid-Treated Montmorillonite Catalysts-A Review", *Applied Clay Science*, 2 (1987) pp. 309–342.

Adams et al., "Clays as Selective Catalysts in Organic Synthesis," *Journal of Inclusion Phenomena*, vol. 5, (1987) pp. 663–674.

"Intercalated Catalysts and Pillared Clays," from Process Evaluation/Research Planning Report by Chem. Systems, Titled "Catalysts: Selected Developments," 84-3, pp. 239–249 (Dec. 1985).

Bolar, "Synthetic Lubricant Base Stocks," Process Economics Program Report No. 125A by SRI International, Apr. 1989 and Supplement A, Sep. 1989.

Kuliev et al., "Preparation of High-Viscosity Synthetic Lubricants Using an Aluminosilicate Catalyst", Institute of Petrochemical Processes of Academy of Sciences of the Azerbaidqhan SSR, *Azerbaid-Zhanskoe, Neftiano, Khozihistvo.*, 1983, No. 4, pp. 40–43.

Chaudhuri and Sharma, "Some Novel Aspects of the Dimerization of α-Methylstyrene with Acidic Ion-Exchange Resins, Clays, and Other Acidic Materials as Catalysts," *Ind Eng. Res.*, vol. 28, pp. 1757–1763 (1989).

Figueras "Pillared Clays as Catalysts", *Catal. Rev. Sci. Eng.*, 30(3), pp. 457–499 (1988).

Dixon and Clark, "Physical Properties of High Molecular Weight Alkylbenzenes and Alkylcyclohexanes," *Journal of Chemical Engineering Data*, vol. 4, No. 1 (Jan. 1959).

R. T. Sanderson, "Viscosity-Temperature Characteristics of Hydrocarbons," Industrial and Engineering Chemistry, vol. 41, No. 2 (Feb. 1949).

O. N. Tsvetkov and M. A. Chagina, "Synthesis and Properties of Alkylnaphthalene Vacuum Pump Oil, " All-Union Scientific Research Institute of Petroleum Processing, Neftepererabotka i Neftekhimiia (Moscow) 1983 (1) pp. 22–23.

Soviet Inventions Illustrated, Section Ch, Week D47, Jan. 8, 1982, Derwent Publications Ltd., London, GB; Class H, P. 2, An 86765 & SU-A-806 667 (Tsvetkov, O. N.) Feb. 23, 1981.

*Primary Examiner*—Prince Willis, Jr.
*Assistant Examiner*—John McNally
*Attorney, Agent, or Firm*—Jack H. Park; Kenneth R. Priem; Russell R. Stolle

[57] ABSTRACT

Synthetic lubricant base stocks having an increased viscosity are disclosed. These synthetic lubricant base stocks comprise a mixture of (1) oligomers prepared from a linear olefin having from 10 to 24 carbon atoms; and (2) alkylated cyclohexanol having an alkyl group containing from 10 to 24 carbon atoms. These synthetic lubricant base stocks may be prepared by hydrogenating the co-reaction products of a linear olefin having from 10 to 24 carbon atoms and phenol.

16 Claims, No Drawings

SYNTHETIC LUBRICANT BASE STOCKS HAVING AN IMPROVED VISCOSITY

CROSS-REFERENCE TO RELATED APPLICATIONS

This application is related to co-pending U.S. patent application Ser. No. 07/500,631, filed Mar. 28, 1990, U.S. Pat. No. 5,053,569 which relates to the preparation of synthetic lubricant base stocks by oligomerizing linear olefins by means of certain acidic montmorillonite clays, and to co-pending U.S. patent application Ser. No. 07/516,931, filed Apr. 30, 1990, which relates to the preparation of synthetic lubricant base stocks by oligomerizing certain mixtures of internal and alpha-olefins by means of certain acidic montmorillonite clays. This application also relates to co-pending U.S. patent application Ser. No. 07/516,870, filed Apr. 30, 1990, U.S. Pat. No. 4,887,970 which relates to synthetic lubricant base stocks made by oligomerizing linear olefins by means of certain aluminum nitrate-treated acidic montmorillonite clays, and to co-pending U.S. patent application Ser. No. 07/522,941, filed May 14, 1990, U.S. Pat. No. 5,105,037 which relates to the preparation of synthetic lubricant base stocks by co-oligomerizing propylene and long-chain alpha-olefins by means of certain acidic montmorillonite clay catalysts. This application also relates to co-pending U.S. patent application Ser. No. 07/525,807, filed May 21, 1990, U.S. Pat. No. 5,030,791 which concerns synthetic lubricant base stocks made by co-oligomerizing 1,3-di-isopropenyl benzene and long-chain alpha-olefins by means of certain acidic montmorillonite clay catalysts, and to co-pending U.S. patent application Ser. No. 07/531,172, filed May 31, 1990, which concerns synthetic lubricant base stocks having an improved pour point. The totality of each of these previously filed applications is incorporated herein by reference.

BACKGROUND OF THE INVENTION

1. Field of the Invention

The invention relates to synthetic lubricant base stocks, and more particularly to synthetic lubricant base stocks having a higher viscosity.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability, with little change in other properties. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of the base stocks generally is determined by the length of the oligomer molecules formed during the oligomerization reaction. The degree of oligomerization is affected b the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_3$ raises environmental concerns. Thus, a method for oligomerizing long-chain olefins using a non-hazardous, non-polluting catalyst would be a substantial improvement in the art.

Kuliev et al. attempted to prepare synthetic lubricants by oligomerizing long-chain ($C_9$–$C_{14}$) olefins using non-hazardous and non-polluting acidic clays comprising sulfuric and hydrochloric acid-activated bentonites from the Azerbaidzhan SSR. See Kuliev, Abasova, Gasanova, Kotlyarevskaya, and Valiev, "Preparation of High-Viscosity Synthetic Lubricants Using an Aluminosilicate Catalyst," Institute of Petrochemical Processes of the Academy of Sciences of the Azerbaidzhan SSR, Azer. Neft. Khoz., 1983, No. 4, pages 40-43. However, Kuliev et al. concluded that "it was not possible to prepare viscous or high-viscosity oils by olefin polymerization over an aluminosilicate catalyst" and that "hydrogen redistribution reactions predominate with formation of aromatic hydrocarbon, coke, and paraffinic hydrocarbon." Gregory et al., on the other hand, used Wyoming bentonite to oligomerize shorter-chain olefins. (See U.S. Pat. No. 4,531,014.) However, like Kuliev et al., they also were unable to obtain a product high in dimer, trimer and tetramer, and low in disproportionation products.

Applicants discovered that it is possible to prepare synthetic lubricant base stocks in good yield by oligomerizing long-chain olefins using certain acidic montmorillonite clay catalysts. Applicants found that a high conversion of long-chain olefin to dimer, trimer, and tetramer may be obtained with formation of very little concomitant hydrogen redistribution by-product by using an acidic calcium montmorillonite clay having a moisture content ranging up to about 20 wt. %, a residual acidity in the range of about 3 to about 30 mg KOH/g (when titrated to a phenolphthalein end point), and a surface area of about 300 $M^2/g$ or greater. In addition to being excellent catalysts, these clays are non-hazardous and non-polluting.

Applicants have discovered that the viscosity of base stocks prepared in this manner may be improved by co-reacting long-chain linear olefins and phenol in the presence of these acidic montmorillonite catalysts. The resulting mixtures of oligomers and alkylated phenols exhibit a viscosity higher than that observed in base stocks comprising the olefin oligomers alone. The incorporation of a hydroxy group (via the phenol) serves to increase the additive solubility of the resulting base stock as well. Additionally, incorporating the phenol lowers the cost of producing the base stocks by replacing a portion of the more expensive long-chain linear olefin feed with phenol. The oligomers and alkylated phenols are hydrogenated (to alkanes and alkylated cyclohexanols) to enhance their oxidative stability.

SUMMARY OF THE INVENTION

In accordance with certain of its aspects, the invention relates to a synthetic lubricant base stock having a higher viscosity, comprising a mixture of (1) reduced oligomers prepared from a linear olefin having from 10 to 24 carbon atoms; and (2) alkylated cyclohexanol having an alkyl group containing from 10 to 24 carbon atoms. In accordance with other of its aspects, the invention relates to a process for preparing synthetic lubricant base stocks having a higher viscosity, comprising the steps of (1) co-reacting phenol and a linear olefin having from 10 to 24 carbon atoms in the presence of an acidic montmorillonite clay; and (2) hydrogenating the resulting mixture of olefin oligomers and alkylated phenols, to obtain a mixture of reduced olefin oligomers and alkylated cyclohexanols.

DESCRIPTION OF THE PREFERRED EMBODIMENTS

Applicants have discovered certain synthetic lubricant base stocks having a higher viscosity, comprising a mixture of (1) oligomers prepared from a linear olefin having from 10 to 24 carbon atoms; and (2) alkylated cyclohexanol having an alkyl group containing from 10 to 24 carbon atoms. Synthetic lubricant base stocks may be prepared in good yield by oligomerizing long-chain linear olefins using certain acidic montmorillonite clay catalysts. The viscosity of these base stocks is improved when the starting materials comprise a mixture of long-chain linear olefin and phenol, preferably from about 1 to about 40 wt. % phenol (i.e. in a weight ratio of phenol to linear olefin of about 1:99 to about 2:3.) More preferably, the mixture of long-chain linear olefin and phenol contains from about 5 to about 25 wt. % phenol (i.e. in a weight ratio of phenol to linear olefin of about 1:20 to about 1:4.) Co-reacting the phenol and linear olefin feed produces a mixture of olefin oligomers and alkylated phenols. The double bonds present in the oligomers and alkylated phenols contained in the mixture are then hydrogenated, to obtain a mixture of reduced oligomers and alkylated cyclohexanols. Preferably, the resulting base stocks contain from about 1 to about 80 wt. % alkylated cyclohexanol. More preferably, the resulting base stocks contain from about 5 to about 40 wt. % alkylated cyclohexanol.

Olefin monomer feed stocks useful in the present invention include compounds comprising (1) alpha-olefins having the formula $R''CH=CH_2$, where $R''$ is an alkyl radical of 8 to 22 carbon atoms, and (2) internal olefins having the formula $RCH=CHR'$, where R and R' are the same or different alkyl radicals of 1 to 20 carbon atoms, provided that the total number of carbon atoms in any one olefin shall be within the range of 10 to 24, inclusive. A preferred range for the total number of carbon atoms in any one olefin molecule is 12 to 18, inclusive, with an especially preferred range being 13 to 16, inclusive. Mixtures of internal and alpha-olefins may be used, as well as mixtures of olefins having different numbers of carbon atoms, provided that the total number of carbon atoms in any one olefin shall be within the range of 10 to 24, inclusive. The alpha and internal-olefins and phenol useful in the present invention may be obtained by processes well-known to those skilled in the art and are commercially available.

Oligomerization of linear olefins may be represented by the following general equation:

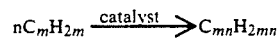

where n represents moles of monomer and m represents the number of carbon atoms in the monomer. Thus, oligomerization of 1-decene may be represented as follows:

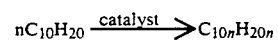

The reactions occur sequentially. Initially, olefin monomer reacts with olefin monomer to form dimers. The dimers that are formed then react with additional olefin monomer to form trimers, and so on. This results in an oligomer product distribution that varies with reaction time. As the reaction time increases, the olefin monomer conversion increases, and the selectivities for the heavier oligomers increase. Generally, each resulting oligomer contains one double bond.

The mono-alkylation of phenol by a linear olefin may be represented as follows:

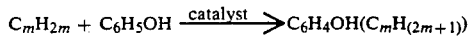

where m = the number of carbon atoms in the olefin monomer. Depending on the mole ratio of linear olefin to phenol and reaction conditions, poly-alkylation of the phenol also will occur. The alkylation of phenol by linear olefin feed occurs concurrently with the oligomerization of the olefin feed. Thus, the co-reaction results in a mixture of oligomers (dimers, trimers, tetramers, etc.) and alkylated phenols, including mono-, di-, and tri-alkylated phenols. The number of carbon atoms in the alkyl groups of the alkylated phenols will correspond to the number of carbon atoms in the linear olefin feed. Thus, the alkyl groups of the alkylated phenols will have from 10 to 24 carbon atoms.

Among the catalysts useful to effect these reactions are certain silica-alumina clays, also called aluminosilicates. Silica-alumina clays primarily are composed of silicon, aluminum, and oxygen, with minor amounts of magnesium and iron in some cases. Variations in the ratios of these constituents, and in their crystal lattice configurations, result in some fifty separate clays, each with its own characteristic properties.

One class of silica-alumina clays comprises smectite clays. Smectite clays have a small particle size and unusual intercalation properties which afford them a high surface area. Smectites comprise layered sheets of octahedral sites between sheets of tetrahedral sites, where the distance between the layers can be adjusted by swelling, using an appropriate solvent. Three-layered sheet-type smectites include montmorillonites. The montmorillonite structure may be represented by the following formula:

$$M_{x/n}^{n+} \cdot yH_2O(Al_{4-x}Mg_x)(Si_8)O_{20}(OH)_4$$

where M represents the interlamellar (balancing) cations, normally sodium or lithium; and x, y and n are integers.

Montmorillonite clays may be acid-activated by such mineral acids as sulfuric acid and hydrochloric acid. Mineral acids activate montmorillonites by attacking and solubilizing structural cations in the octahedral layers. This opens up the clay structure and increases surface area. These acid-treated clays act as strong Bronsted acids. Applicants discovered that certain acid-treated montmorillonite clay catalysts are particularly effective for preparing synthetic lubricant base stocks in good yield by oligomerizing long-chain olefins. These clays are acidic calcium montmorillonite clays having a moisture content ranging up to about 20 wt. %, a residual acidity in the range of about 3 to about 30 mg KOH/g (when titrated to a phenolphthalein end point), and a surface area of about 300 M²/g or greater. Illustrative examples include Filtrol grade 24, having a moisture content of 12 wt. %, a residual acidity of 8.5 mg KOH/g, and a surface area of 425 M²/g; Filtrol grade 124, having a moisture content of 2 wt. %, a residual acidity of 7.0 mg KOH/g, and a surface area of 400 M²/g; Filtrol grade 13, having a moisture content of 16 wt. %, a residual acidity of 15 mg KOH/g, and a surface area of 300 M²/g; Filtrol grade 113, having a moisture content of 4 wt. %, a residual acidity of 10 mg KOH/g, and a surface area of 300 M²/g; and Filtrol grade 224, having virtually no moisture, and having a residual acidity of 3.0 mg KOH/g, and a surface area of 350 M²/g.

Preferably, the clay catalyst is activated by heat treatment before running the co-reactions. Applicants have found that heat treatment of the catalyst prior to running an oligomerization reaction causes the catalyst to be more active and produce a higher olefin conversion. Additionally, clays heat treated in this manner are more stable, remaining active during a reaction for a longer period of time. The clays may be heat treated at temperatures in the range of about 50° to 400° C., with or without the use of a vacuum. A more preferred temperature range is 50° to 300° C. Optionally, an inert gas may be used during heat treatment as well. Preferably, the clay should be heat treated under conditions and for a length of time which will reduce the water content of the clay to approximately 1 wt. % or less.

The oligomerization and alkylation co-reactions may be carried out in either a stirred slurry reactor or in a fixed bed continuous flow reactor. The catalyst concentration should be sufficient to provide the desired catalytic effect. The temperatures at which the oligomerization and alkylation may be performed are between about 50° and 300° C., with the preferred range being about 150° to 180° C. The reactions may be run at pressures of from 0 to 1000 psig.

Following the oligomerization and alkylation co-reactions, the -alkylated phenols and partially unsaturated oligomers are completely reduced via catalytic hydrogenation. Hydrogenation of the oligomers and alkylated phenols improves their thermal stability and helps prevent oxidative degradation during the mixture's use as a lubricant. The hydrogenation reaction for 1-decene oligomers may be represented as follows:

$$C_{10n}H_{20n} + H_2 \xrightarrow{\text{catalyst}} C_{10n}H_{(20n+2)}$$

where n represents moles of monomer used to form the oligomer. The hydrogenation of a mono-alkylated phenol may be represented as follows:

$$C_6H_4OH(C_mH_{(2m+1)}) + H_2 \xrightarrow{\text{catalyst}} C_6H_{10}OH(C_mH_{(2m+1)})$$

Hydrogenation processes known to those skilled in the art may be used. A number of metal catalysts are suitable for promoting the hydrogenation reaction, including nickel, platinum, palladium, copper, and Raney nickel. These metals may be supported on a variety of porous materials such as kieselguhr, alumina, or charcoal. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

Unreacted monomer and phenol should be removed either prior to or after the hydrogenation step. Optionally, unreacted monomer and phenol may be stripped from the oligomers/alkylated phenols prior to hydrogenation and recycled to the catalyst bed for co-reaction. The removal or recycle of unreacted monomer and phenol or, if after hydrogenation, the removal of non-oligomerized alkane and non-alkylated cyclohexanol, should be conducted under mild conditions using vacuum distillation procedures known to those skilled in the art. Distillation at temperatures exceeding 250° C. may cause the oligomers to break down in some fashion and come off as volatiles. Preferably, therefore, the reboiler or pot temperature should be kept at or under about 180° C. Procedures known by those skilled in the art to be alternatives to vacuum distillation also may be employed to separate unreacted components from the oligomer/alkylated phenol mixture.

While it is known to include a distillation step after the hydrogenation procedure to obtain products of various 100° C. viscosities, it is preferred in the method of the present invention that no further distillation (beyond removal of any unreacted monomer/linear alkane and phenol/cyclohexanol) be conducted. Thus, the method of this invention does not require the costly, customary distillation step, yet, surprisingly, produces a synthetic lubricant component that has excellent properties and that performs in a superior fashion. However, in some contexts, one skilled in the art may find subsequent distillation useful in the practice of this invention.

The invention will be further illustrated by the following examples, which are given by way of illustration and not as limitations on the scope of this invention. The entire text of every patent, patent application or other reference mentioned above is hereby incorporated herein by reference.

EXAMPLES

Procedure

Olefin, phenol, and clay catalyst were charged to a three-necked flask equipped with an overhead stirrer, thermometer, heating mantle, and water cooled condenser. A nitrogen purge was used. The mixture was vigorously stirred and heated to the desired temperature for the desired period of time. At the end of the reaction, the mixture was cooled to ambient temperature and filtered with suction.

An autoclave was charged with nickel catalyst (5 wt. %) and the alkylated phenol and oligomer mixture prepared above. The autoclave was then sealed and flushed three or four times with hydrogen. The autoclave was then pressured to 1000 psig with hydrogen and heated to 200° C. The mixture was stirred at this temperature for 4.0 hours. The autoclave was repressured to 2000 psig as needed. The mixture was then cooled to ambient temperature and filtered. Unreacted monomer was then removed from the filtrate under vacuum distillation (approx. 1 mm Hg). The properties shown in the table below were determined on the "stripped" bottoms product.

atoms, wherein the mixture contains from about 1 to about 80 wt. % of said alkylated cyclohexanol.

2. The synthetic lubricant base stock of claim 1, wherein the mixture contains from about 5 to about 40 wt. % alkylated cyclohexanol.

3. The synthetic lubricant base stock of claim 1, wherein the reduced oligomers and alkylated cyclohexanol comprise hydrogenated co-reaction products of a linear olefin having from 10 to 24 carbon atoms and phenol.

4. The synthetic lubricant base stock of claim 1, wherein the mixture has a viscosity greater than about 9 centistoke.

5. A synthetic lubricant base stock having an increased viscosity, comprising a mixture of (1) oligomers prepared from a linear olefin having from 12 to 18 carbon atoms; and (2) alkylated cyclohexanol having an alkyl group containing from 12 to 18 carbon atoms, wherein the mixture contains from about 5 to about 40 wt. % of said alkylated cyclohexanol.

6. The synthetic lubricant base stock of claim 5, wherein the oligomers and alkylated cyclohexanol comprise hydrogenated co-reaction products of a linear olefin having from 12 to 18 carbon atoms and phenol.

7. A process for preparing synthetic lubricant base stocks having an increased viscosity, comprising the steps of (1) co-reacting phenol and a linear olefin having from 10 to 24 carbon atoms in a weight ratio of phenol to linear olefin of about 1:99 to about 2:3 in the presence of an acidic montmorillonite clay having a moisture content ranging up to about 20 wt. %, a residual acidity in the range of about 3 to about 30 mg KOH/g, and a surface area of about 300 m$^2$/g or greater; and (2) hydrogenating the mixture resulting from step (1), to obtain a mixture comprising reduced olefin oligomers and alkylated cyclohexanols.

8. The process of claim 7, wherein the phenol and linear olefin of step (1) are co-reacted in a weight ratio of phenol to linear olefin of about 1:20 to about 1:4.

9. The process of claim 7, wherein the linear olefin of step (1) has from 12 to 18 carbon atoms.

10. The process of claim 7, further comprising the

| | | CO-REACTION OF OLEFINS AND PHENOL | | | | Properties After Hydrogenation | | | |
|---|---|---|---|---|---|---|---|---|---|
| Ex. No. | Reactants | (g) of Reactants | Harshaw/ Filtrol Catalyst | (g) of Catalyst | Time/Temp (Hr)/(°C.) | Con. (%) of Olefin | % Remaining by TGA (250° C.) | VIS (cSt) @ 210° F. | VI | Pour Point (°F.) |
| 1 | C-14A/Phenol | 360/40 | H/F Clay 124 | 40 | 5/160 | 85 | 96.1 | 9.47 | 104 | −30 |
| 2 | C-14A/Phenol | 320/80 | Dried H/F Clay 124 | 40 | 2/160 | 98 | 90.8 | 8.97 | 97 | −20 |
| 3 | C-15I, 18I/Phenol | 320/80 | Dried H/F Clay 13 | 40 | 5/160 | 93 | 91.5 | 9.85 | * | −10 |
| 4 | C-14A, 16A/Phenol | 320/80 | Dried H/F Clay 13 | 40 | 5/160 | 98 | 92.2 | 9.64 | * | −15 |
| 5 | C-15I, 18I/Phenol | 320/80 | Dried H/F Clay 13 | 40 | 2/160 2/180 | 94 | 91.9 | 9.63 | * | −15 |
| 6 | C-14A16A/Phenol | 320/80 | Dried H/F Clay 13 | 40 | 2/160 2/180 | 97 | 93.0 | 9.71 | * | −10 |
| 7 | C-14A | 400 | H/F Clay 13 | 20 | 5/150 | 68 | 82.1 | 4.36 | 134 | −20 |

Con. = Conversion; A = Alpha; I = Internal; TGA = Thermogravimetric Analysis; VIS = Viscosity; VI = Viscosity Index; * = not determined.

We claim:

1. A synthetic lubricant base stock having an increased viscosity, comprising a mixture of (1) reduced oligomers prepared from a linear olefin having from 10 to 24 carbon atoms; and (2) alkylated cyclohexanol having an alkyl group containing from 10 to 24 carbon step of (3) removing from the mixture resulting from step (2) any non-oligomerized alkane and non-alkylated cyclohexanol.

11. The process of claim 7, wherein the acidic montmorillonite clay is an acidic calcium montmorillonite clay having a moisture content of about 16 wt. %, a residual acidity of about 15 mg KOH/g, and a surface area of about 300 M²/g or greater.

12. A process for preparing synthetic lubricant base stocks having an increased viscosity, comprising the steps of (1) co-reacting phenol and a linear olefin having from 10 to 24 carbon atoms in a weight ratio of phenol to linear olefin of about 1:99 to about 2:3 in the presence of an acidic montmorillonite clay having a moisture content ranging up to about 20 wt. %, a residual acidity in the range of about 3 to about 30 mg KOH/g, and a surface area of about 300 m²/g or greater; (2) removing from the mixture resulting from step (1) any non-oligomerized linear olefin and non-alkylated phenol; and (3) hydrogenating the mixture resulting from step (2), to obtain a mixture of reduced olefin oligomers and alkylated cyclohexanols.

13. The process of claim 12, wherein the phenol and linear olefin of step (1) are co-reacted in a weight ratio of phenol to linear olefin of about 1:20 to about 1:4.

14. The process of claim 12, wherein the linear olefin of step (1) has from 12 to 18 carbon atoms.

15. The process of claim 12, wherein the acidic montmorillonite clay is an acidic calcium montmorillonite clay having a moisture content of about 16 wt. %, a residual acidity of about 15 mg KOH/g, and a surface area of about 300 M²/g or greater.

16. The process of claim 12, wherein the non-oligomerized linear olefin and non-alkylated phenol removed in step (2) are recycled and co-reacted as in step (1).

* * * * *